Figure 1:
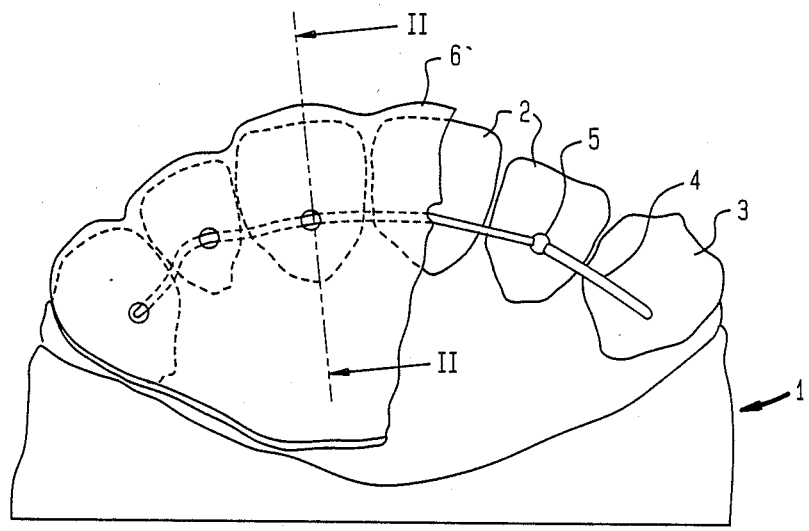

United States Patent [19]

Guis

[11] Patent Number: 4,932,866
[45] Date of Patent: Jun. 12, 1990

[54] METHOD OF APPLYING AN ORTHODONTIC AID

[76] Inventor: Marinus B. Guis, A. Volkersingel 13, 3361 HA Sliedrecht, Netherlands

[21] Appl. No.: 230,337

[22] Filed: Aug. 9, 1988

[30] Foreign Application Priority Data

Aug. 11, 1987 [NL] Netherlands .......................... 8701879

[51] Int. Cl.$^5$ ............................................... A61C 7/00
[52] U.S. Cl. ..................................................... 433/24
[58] Field of Search ............................... 433/24, 6, 5, 7

[56] References Cited

U.S. PATENT DOCUMENTS

| | | | |
|---|---|---|---|
| 3,949,477 | 4/1976 | Cohen | 433/24 |
| 4,516,938 | 5/1985 | Hall | 433/215 |
| 4,609,349 | 9/1986 | Cain | 433/7 |

Primary Examiner—Robert Peshock
Attorney, Agent, or Firm—Peter L. Michaelson

[57] ABSTRACT

A method of applying an orthodontic wire which is affixed to at least one of a row of teeth with an adhesive. A cast is made of the row of teeth. The wire is brought into the desired shape on the cast, and temporarily secured in position. Over the cast with wire, a layer of permanently resilient material is applied, which is deformed to conform to the shape of the cast to form a mold. The mold with the wire embedded therein is removed from the mold. The wire is temporarily removed from the mold, the mold is provided with perforations at the desired locations, which correspond to the shape and dimensions of the adhesive receiving places, the wire is re-positioned in the mold, and the perforations are filled with adhesive. The mold with the wire embedded therein and adhesive applied is then placed on, and over, the row of teeth and pressed into contact with them. Any excess of adhesive pressed out of the perforations is removed, and the pressure is maintained until the adhesive has set on the row of teeth and secures the wire relatively to the row of teeth. The mold is then removed, leaving the wire affixed to the row of teeth.

5 Claims, 1 Drawing Sheet

METHOD OF APPLYING AN ORTHODONTIC AID

This invention relates to a method of applying an orthodontic aid which is affixed to at least one of a row of teeth by means of an adhesive. A prior method of applying an orthodontic aid in this way is disclosed in U.S. Pat. No. 3,738,005, and comprises making a cast of said row of teeth by means of the mold and counter-mold method;

temporarily securing the aid to the cast at the desired location;

applying over the cast with the aid a layer of a material which remains resilient, and deforming it to conform to the shape of the cast to form a mold;

removing the mold with embedded aid from the cast;

placing the mold with embedded aid and applied adhesive on, and over, said row of teeth, and holding it in contact therewith until the adhesive has adhered to the row of teeth and secures the aid relatively to the row of teeth; and removing the mold, leaving the aid affixed to the row of teeth.

The U.S. patent is concerned with applying to a number of teeth supports for securing further orthodontic aids. By using the mold and counter-mold method, the time a patient has to be available can be advantageously shortened, and by using the cast, the relative position of the supports and the position of a support relative to the teeth to which it is to be secured can be fixed in a reliable and accurate manner, at least in principle.

The supports referred to are often provided with a concavo-convex surface facing the tooth. The adhesive should be applied to that surface before the mold is placed on the row of teeth. Too little adhesive will of course give insufficient adherence. Accordingly, care will be taken that this does not happen. This implies, however, that almost always an excess of adhesive is applied. When the mold is pressed onto the row of teeth, the excess of adhesive may give rise to problems. The excess of adhesive will either be pressed in between the support and the tooth, or prevent the support from coming into contact with the tooth in the correct, desirable manner. This latter effect results in malpositioning of the support in spite of the use of the mold. Pressing the excess of adhesive between tooth and support results in the formation of irregular adhesive flashes on the teeth, in which connection it should be borne in mind that the mold cannot be removed until after the adhesive, and hence each projection, has hardened. In this way, the time saved by using mold and cast can be largely lost due to long finishing and after-treatments in the patient's mouth. For that matter, even such additional operations do not always lead to an optimum esthetic result.

It is an object of the present invention to provide a method of applying an orthodontic aid which does not have the above problems.

This is achieved, in accordance with the present invention, in a method of the above kind, by the improvement which comprises that the aid is a wire, which is formed into the desired shape on the cast;

the wire is temporarily removed from the mold after being removed from the cast;

the mold is provided at the desired locations with perforations corresponding to the shape and dimensions of the adhesive receiving places;

the wire is re-positioned in the mold; and the perforations are filled up with adhesive, whereafter the mold is placed over the row of teeth and any excess of adhesive pressed out of the perforations on the outside of the mold is removed.

As a result of these features, first of all the time which the patient should be available is minimized, while such time is also fixed within reasonably narrow limits. This is a result of the streamlining of the actual application treatment by using the mold with embedded wire and filling the perforations with adhesive. This latter feature has the additional advantages that the amount of adhesive required and applied can be accurately dosed, that any excess of adhesive is pressed through the perforations out of the mold on the side remote from the row of teeth and thus can be readily removed, and that the shape which the adhesive has after setting is pre-determined. In addition to all this, there are the advantages obtained as a result of a reduced risk of misshaped adhesive spots and errors during an after-treatment required by reason of an excess or a shortage of adhesive, while the required shorter real time of treatment will be attractive to the patient. Moreover, the deliberate use of a slight excess of adhesive will ensure that the perforations are always completely filled up, so that, on this point, too, any after-treatments are prevented in a reliable manner.

In accordance with a further embodiment of the present invention, the wire is provided with forming members before the resilient layer is applied, which forming members, during the application and deformation of the resilient layer, define the place, shape and dimensions of the desired perforations, and are removed, after the deformation of the resilient layer, from the mold then formed to realize the perforations. In this case the forming members can also serve for keeping the wire in position during the formation of the mold. Another way of achieving this effect is obtained, in accordance with a further embodiment of the invention, by fixing the wire on the cast with at least two wax droplets before the resilient layer is applied.

In order to ensure optimum securement of the wire to the teeth, it is preferable, and in accordance with a further embodiment of the invention, that the perforations have a frustoconical shape with the base surface of the cone being contained in the surface of the mold which comes into, or is in, contact with the tooth surfaces to which the wire must be affixed.

The resilient layer can be deformed into the desired mold in many ways, possibly depending on the material used. In accordance with a further embodiment of the invention, however, it is preferred that the deformation of the resilient layer is effected through causing said layer to bed down snugly on to the cast with wire by vacuum suction. It has been found that in this way an extremely accurately shaped mold can be made.

Figure 2:
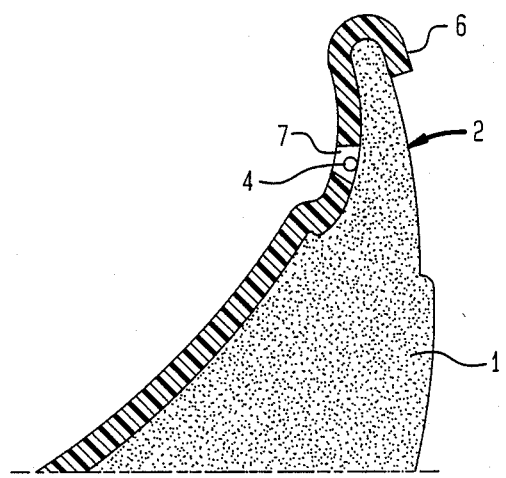

The method of applying an orthodontic wire according to the invention will now be described and elucidated in more detail with reference to an embodiment shown, by way of example, in the accompanying drawings. In said drawings, FIG. 1 shows an elevational view of the inside of a cast of a row of teeth with a mold conforming to it in shape, and partly cut away, and an appropriately shaped wire; and FIG. 2 shows a cross-sectional view taken on the line II—II of FIG. 1.

Referring to the drawings, there is shown a cast 1 of a row of teeth, comprising four incisors 2 and two eye-teeth 3, obtained in a conventional manner by the mold and counter-mold method. A wire 4 is deformed on cast 1 until it follows the inner contour of the row of teeth 2, 3 as desired. Subsequently to this operation, wire 4 is fixed in the desired position relative to the row of teeth, for example, with a droplet of wax 5 at two spaced positions. A layer of permanently resilient material is laid over the cast 1 with wire 4, thus produced, and deformed in a manner appropriate for that material, for example, by means of vacuum suction or a heat treatment, in such a manner that the layer beds down snugly on cast 1 with wire 4, so that wire 4 is embedded in the later, which is thus formed into a mold 6.

Mold 6 with the embedded wire 4 are removed from cast 1, whereafter, in turn, wire 4 is removed from mold 6. Perforations are provided in mold 6, which form the mirror image of the ultimately desired points of attachment of wire 4 on the row of teeth. As the mold 6 has, in mirror image, the shape of the row of teeth and the wire 4 to be secured to these, the place, shape and dimensions of the points of attachment to be formed can be fixed extremely accurately. In the embodiment shown by way of example in FIG. 2, the perforations 7 are of frustoconical configuration, with the larger base surface of the cone on the side of mold 6 which when placed on the row of teeth will come into contact with the inner surface of the teeth.

As stated before, before forming mold 6, wire 4 is fixed on cast 1, for example, with two drops of wax 5. These drops can be provided at the positions where subsequently perforations are provided. It is also possible to realize the fixation of wire 4 prior to the formation of mold 6 in such a manner and by such means that when wire 4 with its fixing means are removed from the formed mold 6, the desired perforations are automatically obtained therein. It will be understood, for that matter, that the perforations may have any desired shape, size and position.

After providing the perforations, in the example the frustoconical perforations 7, the wire 4 is re-positioned in mold 6, and mold 6 and wire 4 are thus ready for the actual positioning treatment of the wire 4 on the row of teeth.

It will be clear that, except for the making of the initial impression of the row of teeth, all of the above operations can be carried out without requiring the patient's presence. Indeed, the performance of these operations is not bound to any particular place, and thus can take place where possible in the most efficient and least expensive manner.

The actual positioning treatment begins with filling the perforations 7 formed in mold 6 with adhesive. The amount of adhesive to be applied can thus be accurately dosed. Mold 6 with the wire 4 embedded therein, and with the perforations 7 filled with adhesive is placed over the row of teeth in the patient's mouth, and pressed and held in the desired position until the adhesive has a desired degree of setting. While the combination is pressed down, the adhesive filling perforations 7 is pressed on one side against the surfaces of attachment on the teeth, and at the other side wire 4 is enveloped by adhesive in the desired manner at the points of attachment. The frustoconical configuration of perforations 7 ensures proper densification and complete filling of perforations 7, while any excess of adhesive can escape outwardly, thereby effectively preventing that, even in case too much adhesive has been used, the adhesive penetrates between mold 6 and the teeth outside the points of attachment contemplated.

After removing any set adhesive pressed outwardly through perforations 7, mold 6 can be removed from the row of teeth, leaving wire 4 attached to the row of teeth. If desired, the upper surfaces of the points of attachment of wire 4 can be rounded, which completes the positioning treatment.

It will be clear that many modifications and variants can be made without departing from the scope of the invention. As stated before, the perforations can be designed and provided in many ways. For the mold, any suitable material can be chosen, which can be brought into the desired shape conforming to the cast in any suitable manner. Although the invention has been described with particular reference to a wire or the wire, the method is equally applicable to the positioning of more than one wire or wires consisting of separate parts which may or may not be subsequently coupled together by means of special elements. The same applies to correctional means of the present type which are not generally indicated as wires.

What I claim is:

1. In a method of applying an orthodontic aid which is affixed to at least one of a row of teeth with an adhesive, and which comprises:
    making a cast of said row of teeth by means of the mold and counter-mold method;
    temporarily securing the aid to the cast at the desired location;
    applying over the cast including the aid a layer of a permanently resilient material, and deforming it to conform to the shape of the cast to form a mold;
    removing the mold with the aid embedded therein from the cast;
    placing the mold with the aid embedded therein and applied adhesive on, and over, said row of teeth and holding it in contact therewith until the adhesive has adhered to the row of teeth and secures the aid relatively to the row of teeth; and
    removing the mold, leaving the aid affixed to the row of teeth,
the improvement which comprises that
    the aid is a wire which is formed into the desired shape on the cast;
    the wire is temporarily removed from the mold after being removed from the cast;
    the mold is provided at the desired locations with perforations corresponding to the shape and dimensions of the adhesives receiving places;
    the wire is re-positioned in the mold; and
    the perforations are filled up with adhesive, whereafter the mold is placed over the row of teeth and any excess of adhesive pressed out to the perforations on the outside of the mold is removed.

2. A method as claimed in claim 1, wherein, before applying the resilient layer, the wire is provided with forming members which during the application and deformation of the resilient layer define the plate, shape and dimensions of the desired perforations, which forming members are removed, after the deformation of the resilient layer, from the mold then formed to realize the perforations.

3. A method as claimed in claim 1 wherein the wire is fixed on the cast with at least two wax droplets before the resilient layer is applied.

4. A method as claimed in claim 1, wherein the perforations have a frustoconical shape with the base surface of the cone being contained in the surface of the mold which comes into contact with the tooth surfaces to which the wire must be affixed.

5. A method as claimed in claim 1, wherein the deformation of the resilient layer is effected through causing said layer to bed down snugly on to the cast with wire by vacuum suction.

* * * * *